(12) United States Patent
Nagamine et al.

(10) Patent No.: US 6,407,121 B1
(45) Date of Patent: Jun. 18, 2002

(54) ARYLPIPERIDINE DERIVATIVES AND USE THEREOF

(75) Inventors: Masashi Nagamine; Makoto Gotoh; Masanori Yoshida, all of Kawachinagano; Atsuro Nakazato, Tokyo; Toshihito Kumagai, Tokyo; Shigeyuki Chaki, Tokyo; Kazuyuki Tomisawa, Tokyo, all of (JP)

(73) Assignees: Nihon Nohyaku Co., Ltd.; Taisho Pharmaceutical Co., Ltd., both of Tokyo (JP)

( * ) Notice: Subject to any disclaimer, the term of this patent is extended or adjusted under 35 U.S.C. 154(b) by 0 days.

(21) Appl. No.: 09/646,080

(22) PCT Filed: Mar. 19, 1998

(86) PCT No.: PCT/JP98/01180

§ 371 (c)(1),
(2), (4) Date: Sep. 13, 2000

(87) PCT Pub. No.: WO99/47515

PCT Pub. Date: Sep. 23, 1999

(51) Int. Cl.[7] .................... A61K 31/445; C07D 401/00; C07D 411/00; C07D 421/00
(52) U.S. Cl. ................ 514/320; 514/323; 514/324; 546/201; 546/202; 546/196
(58) Field of Search ................. 546/201, 196, 546/202; 514/323, 324, 256, 320; 544/333

(56) References Cited

U.S. PATENT DOCUMENTS 4,100,291 A * 7/1978 Clemence et al. .......... 424/267
5,059,601 A 10/1991 Salimbeni et al.
5,066,660 A * 11/1991 Oxford et al.
5,684,020 A 11/1997 Peglion et al.
5,693,655 A 12/1997 Bottcher et al.
5,714,498 A 2/1998 Kulagowski et al.

FOREIGN PATENT DOCUMENTS

| JP | 2-240068 | 9/1990 |
| JP | 4-352770 | 12/1992 |
| JP | 7-291969 | 11/1995 |
| JP | 8-508030 | 8/1996 |
| JP | 8-325257 | 12/1996 |

* cited by examiner

Primary Examiner—Alan L. Rotman
Assistant Examiner—Binta Robinson
(74) Attorney, Agent, or Firm—Paul E. White, Jr.; Manelli Denison & Selter PLLC

(57) ABSTRACT

The present invention provides an arylpiperidine derivative of the formula (I) or a pharmaceutically acceptable salt thereof, which has antipsychotic effect:

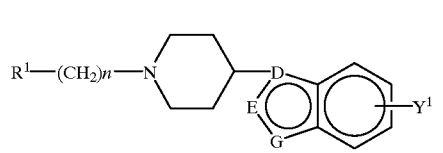

(I)

wherein D is a carbon atom or a nitrogen atom, E is a CH group or a nitrogen atom, G is an oxygen atom, a sulfur atom, a nitrogen atom or an NH group, $Y^1$ is a hydrogen atom or a halogen atom, n is an integer of 1 to 4, and $R^1$ is a group represented by any of the formulas (i) to (iv) defined in the specification.

13 Claims, No Drawings

ARYLPIPERIDINE DERIVATIVES AND USE THEREOF

This application is a 371 of PCT/JP98/01180 filed Mar. 19, 1998 which claims benefit of Ser. No. 08/249,699 filed May 26, 1994 Pat. No. 5,496,427.

TECHNICAL FIELD

The present invention relates to arylpiperidine derivatives having antipsychotic effect.

BACKGROUND ART

Antipsychotic agents are used not only for treating schizophrenia but also for treating problem behaviors associated with cerebrovascular diseases or senile dementia (e.g. aggressive behaviors, psychogenic excitement, ecdemomania and delirium). However, dopamine $D_2$ receptor antagonists, conventional antipsychotic agents, cause serious extrapyramidal diseases as side effects, which has been a serious problem.

On the other hand, recently found dopamine $D_4$ receptors are similar to dopamine $D_2$ receptors in structure and properties but are utterly different from dopamine $D_2$ receptors in intracerebral distribution. The intracerebral distribution of dopamine $D_4$ receptors is such that they are present in a high concentration in cerebral cortex frontal lobe concerned with the onset of schizophrenia and are present in a low concentration in striatum involved in the onset of extrapyramidal diseases. Therefore, unlike the dopamine $D_2$ receptor antagonists, dopamine $D_4$ receptor antagonists are very likely to become novel therapeutic agents for schizophrenia which do not cause extrapyramidal diseases as side effects (Nature, 350, 610–614(1991); Nature, 358, 109 (1992); Nature 365, 393(1993); Nature 365, 441–445 (1993)).

As such a compound, there is clozapine. It has been reported that the affinity of clozapine for dopamine $D_4$ receptors is higher than that for dopamine $D_2$ receptors (Nature, 350, 610–614(1991)). It has also been reported that in clinical investigation of clozapine, unlike the dopamine $D_2$ receptor antagonists, clozapine is effective on drug-resistant schizophrenia and negativism and hardly causes extrapyramidal diseases (Arch. Gen. Psych., 45, 789–796 (1988)). Clozapine, however, causes a blood disease called agranulocytosis and deaths due to this disease have been reported (Summary and Clinical Data. Sandoz, Canada Inc. (1990)), and this is an serious defect of clozapine.

Accordingly, dopamine $D_4$ receptor antagonists which do not have such a side effect are very useful as therapeutic agents for schizophrenia and the like which are very unlikely to cause extrapyramidal diseases.

DISCLOSURE OF THE INVENTION

An object of the present invention is to provide a dopamine $D_4$ receptor antagonistic compound which has antipsychotic effect without causing extrapyramidal diseases.

The present inventors earnestly investigated arylpiperidine derivatives and consequently found novel arylpiperidine derivatives having a high affinity for dopamine $D_4$ receptors, whereby the present invention has been accomplished.

The present invention is explained below.

The present invention is an arylpiperidine derivative represented by the formula (I):

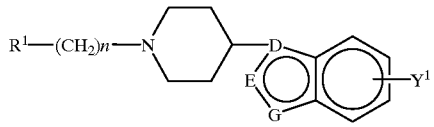

(I)

[wherein D is a carbon atom or a nitrogen atom, E is a CH group or a nitrogen atom, G is an oxygen atom, a sulfur atom, a nitrogen atom or an NH group, $Y^1$ is a hydrogen atom or a halogen atom, n is an integer of 1 to 4, and $R^1$ is a group represented by the formula (i):

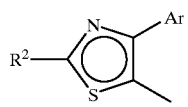

(i)

(wherein $R^2$ is a hydrogen atom, an alkyl group of 1 to 5 carbon atoms, an amino group, a monoalkylamino group of 1 to 5 carbon atoms, a hydroxyl group, an alkoxycarbonyl group of 2 to 6 carbon atoms, a carbamoyl group, a carboxyl group, or a metal salt of carboxyl group, and Ar is a substituted or unsubstituted phenyl group or a thienyl group), a group represented by the formula (ii):

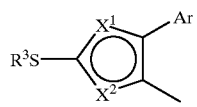

(ii)

(wherein $R^3$ is an alkyl group of 1 to 5 carbon atoms, each of $X^1$ and $X^2$, which are different from each other, is a nitrogen atom or an NH group, and Ar is a substituted or unsubstituted phenyl group or a thienyl group), a group represented by the formula (iii):

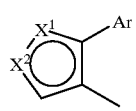

(iii)

(wherein $X^1$ and $X^2$ are as defined above, and Ar is a substituted or unsubstituted phenyl group or a thienyl group), or a group represented by the formula (iv):

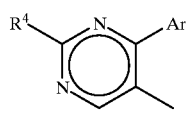

(iv)

(wherein $R^4$ is a hydrogen atom, a mercapto group, or an alkylthio group of 1 to 5 carbon atoms, and Ar is a substituted or unsubstituted phenyl group or a thienyl group)] or a pharmaceutically acceptable salt thereof.

In the present invention, the substituted phenyl group refers to a phenyl group having one or two substituents selected from halogen atoms, alkyl groups of 1 to 5 carbon atoms, alkoxy groups of 1 to 5 carbon atoms and trifluoromethyl group, and is, for example, a 2-fluorophenyl group, 3-fluorophenyl group, 4-fluorophenyl group, 4-chlorophenyl group, 4-bromophenyl group, 3,4-dichlorophenyl group, 4-methylphenyl group, 3,4-dimethylphenyl group, 4-methoxyphenyl group, 3,4-dimethoxyphenyl group, 2-trifluoromethylphenyl group, 3-trifluoromethylphenyl group or 4-trifluoromethylphenyl group.

The halogen atom is a fluorine atom, chlorine atom, bromine atom or iodine atom.

The alkyl group of 1 to 5 carbon atoms is a linear, branched or cyclic alkyl group such as methyl, ethyl, propyl, isopropyl, butyl, isobutyl, sec-butyl, t-butyl, cyclopropylmethyl, pentyl, isopentyl or the like.

The alkoxy group of 1 to 5 carbon atoms is a linear or branched alkoxy group such as methoxy, ethoxy, propoxy, isopropoxy, butoxy, isobutoxy, t-butoxy, pentoxy, 3-methylbutoxy or the like.

The monoalkylamino group of 1 to 5 carbon atoms is, for example, a methylamino group, ethylamino group, propylamino group, isopropylamino group or the like.

The alkylthio group of 1 to 5 carbon atoms is, for example, a methylthio group, ethylthio group, propylthio group, isopropylthio group, butylthio group, isobutylthio group or the like.

The alkoxycarbonyl group of 2 to 6 carbon atoms is, for example, a methoxycarbonyl group, ethoxycarbonyl group, propoxycarbonyl group, isopropoxycarbonyl group, butoxycarbonyl group or the like.

The pharmaceutically acceptable salt of the present invention is, for example, a salt with a mineral acid such as sulfuric acid, hydrochloric acid, phosphoric acid or the like, or a salt with an organic acid such as acetic acid, oxalic acid, lactic acid, tartaric acid, fumaric acid, maleic acid, trifluoroacetic acid, methanesulfonic acid, pamoic acid, decanoic acid, enanthic acid or the like.

Arylpiperidine derivatives of the formula (I) in which $R^1$ is represented by the formula (ii) or (iii) have tautomers due to their chemical structures, and the present invention includes these tautomers.

The compound of the present invention is preferably an arylpiperidine derivative represented by the formula (II):

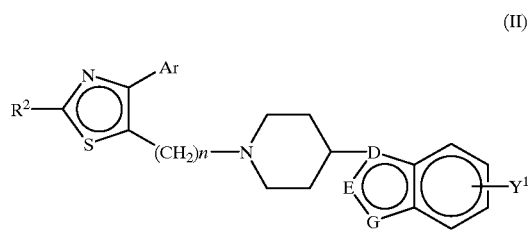

(II)

(wherein $R^2$, $Y^1$, D, E, G, $Y^1$ and n are as defined above) or a pharmaceutically acceptable salt thereof.

Said compound is more preferably an arylpiperidine derivative represented by the formula

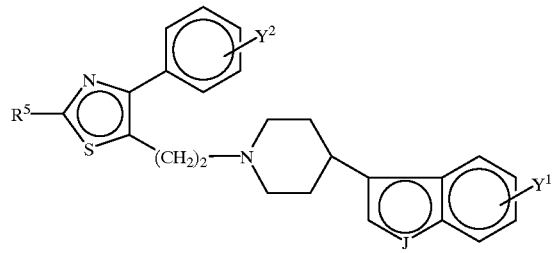

(III)

wherein $Y^1$ is as defined above, $Y^2$ is a hydrogen atom or a halogen atom, J is an oxygen atom, a sulfur atom or an NH group, and $R^5$ is an alkyl group of 1 to 5 carbon atoms, an amino group or a carbamoyl group) or a pharmaceutically acceptable salt thereof.

The compound of the formula (I) can be produced by any of the following processes.

In the following reaction formulas, Ar, D, E, G, $R^3$, $R^4$, $X^1$, $X^2$, $Y^1$ and n are as defined in the above formula (I), $R^6$ is a hydrogen atom, an alkyl group of 1 to 5 carbon atoms, an amino group, or a monoalkylamino group of 1 to 5 carbon atoms, $R^7$ and $R^8$ are taken together with the adjacent nitrogen atom to represent a pyrrolidino group, a piperidino group, a morpholino group, an N-methylpiperazino group or the like, Z is a chlorine atom, a bromine atom or an iodine atom, $M^1$ is, for example, sodium, potassium or $NH_4$, and $M^2$ is an alkali metal ion (e.g. sodium, potassium, lithium or calcium), an alkaline earth metal ion or a hydrogen atom.

(Reaction formulas 1)

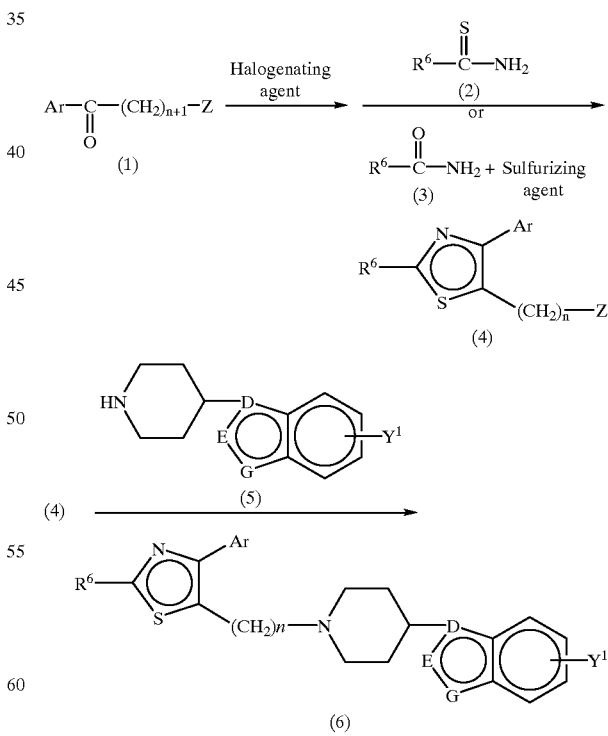

A ketone derivative (1) is halogenated with a halogenating agent in an inert solvent and then reacted with a thiourea derivative or thioamide derivative of the formula (2) or with a urea derivative or amide derivative of the formula (3) and a sulfurizing agent, in an inert solvent in the presence or absence of a dehydrating agent to obtain a compound (4). Subsequently, the compound (4) is reacted with a piperidine derivative of the formula (5) in an inert solvent in the presence of a base to obtain a compound (6) of the present invention.

In each of these reactions, the inert solvent is, for example, an organic carboxylic acid such as acetic acid; an organic halide such as chloroform or carbon tetrachloride; an alcohol such as ethanol or isopropanol; an ether such as tetrahydrofuran or dioxane; a hydrocarbon such as benzene or toluene; a ketone compound such as acetone or methyl ethyl ketone; N,N-dimethylformamide; acetonitrile; water; or a mixed solvent thereof. The halogenating agent is, for example, chlorine, bromine, iodine or sulfuryl chloride.

The dehydrating agent is, for example, a molecular sieves such as molecular sieves 3A or molecular sieves 4A; an inorganic salt such as anhydrous magnesium sulfate, anhydrous calcium sulfate or anhydrous calcium chloride; or phosphorus pentaoxide. The sulfurizing agent is, for example, phosphorus pentasulfide or Lawesson's reagent. The base is, for example, an organic amine such as triethylamine, diisopropylethylamine or pyridine; an alcoholate such as sodium ethoxide; an alkali metal amide such as sodium amide; an inorganic base such as sodium hydrogencarbonate, sodium carbonate, potassium carbonate, sodium hydroxide or sodium hydride; or an organic acid salt such as sodium acetate.

dimethylformamide; acetonitrile; water; or a mixed solvent thereof. The acid treatment is treatment with one of or a mixture of two or more of acids such as hydrochloric acid, sulfuric acid, acetic acid, trifluoroacetic acid, methanesulfonic acid, p-toluenesulfonic acid, etc. in an alcohol (e.g. methanol or ethanol), an ether (e.g. dioxane) or water.

Then, the compound (8) is reacted with a piperidine derivative (5) in an inert solvent in the presence of a base to obtain a compound (9) of the present invention.

In this reaction, the inert solvent is, for example, an alcohol such as ethanol or isopropanol; an ether such as tetrahydrofuran or dioxane; a hydrocarbon such as benzene or toluene; a ketone compound such as acetone or methyl ethyl ketone; N,N-dimethylformamide; acetonitrile; water; or a mixed solvent thereof. The base is, for example, an organic amine such as triethylamine, diisopropylethylamine or pyridine; an alcoholate such as sodium ethoxide; an alkali metal amide such as sodium amide; an inorganic base such as sodium hydrogencarbonate, sodium carbonate, potassium carbonate, sodium hydroxide or sodium hydride; or an organic acid salt such as sodium acetate.

(Reaction formulas 2)

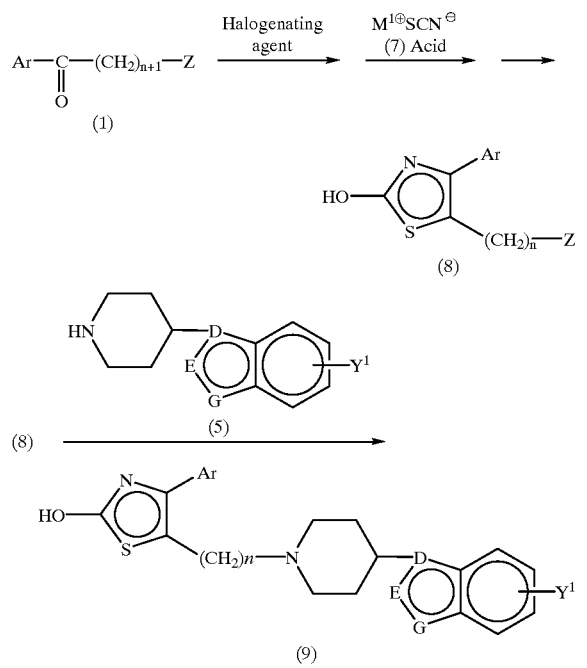

(Reaction formulas 3)

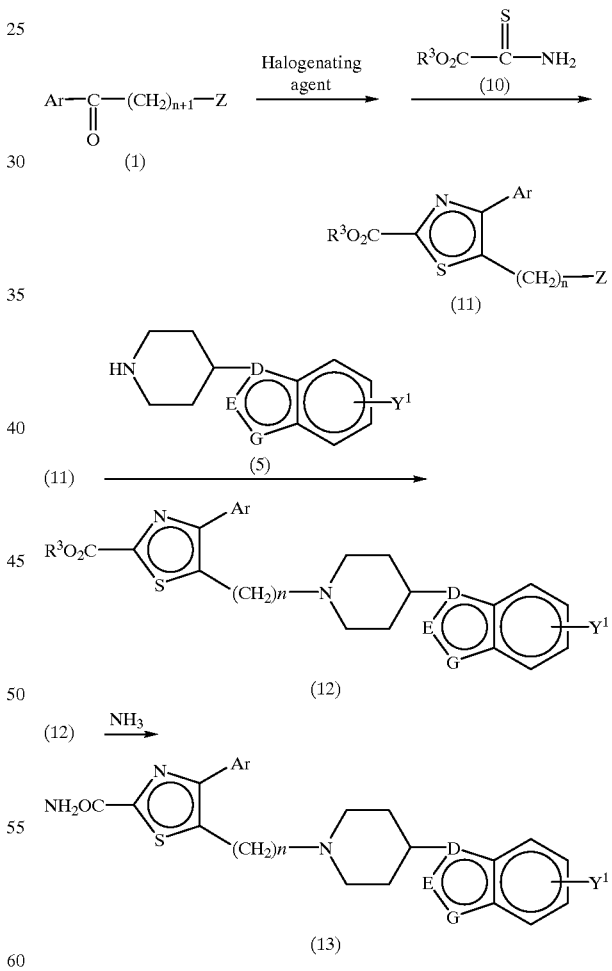

A ketone derivative (1) is halogenated with a halogenating agent in the same manner as in the reaction formulas 1 and reacted with a thiocyanate (7) in an inert solvent, and the reaction product is subjected to acid treatment to obtain a 2-hydroxythiazole derivative (8).

In the reaction, the inert solvent is, for example, an organic carboxylic acid such as acetic acid; an organic halide such as carbon tetrachloride or chloroform; an alcohol such as ethanol or isopropanol; an ether such as diethyl ether or tetrahydrofuran; a hydrocarbon such as toluene; N,N-

A ketone derivative (1) is hydrogenated with a hydrogenating agent in the same manner as in the reaction formulas 1 and then reacted with a thioamide derivative (10) in an inert solvent in the presence or absence of a dehydrating agent to obtain a thiazole derivative (11). Subsequently, the compound (11) is reacted with a piperidine derivative (5) in an inert solvent in the presence of a base to obtain a compound (12) of the present invention.

In each of these reactions, the inert solvent is, for example, an alcohol such as ethanol or isopropanol; an ether such as tetrahydrofuran or dioxane; a hydrocarbon such as benzene or toluene; a ketone compound such as acetone or methyl ethyl ketone; N,N-dimethylformamide; acetonitrile; water; or a mixed solvent thereof. The base is, for example, an organic amine such as triethylamine, diisopropylethylamine or pyridine; an alcoholate such as sodium ethoxide; an alkali metal amide such as sodium amide; an inorganic base such as sodium hydrogencarbonate, sodium carbonate, potassium carbonate, sodium hydroxide or sodium hydride; or an organic acid salt such as sodium acetate.

The compound (12) can be converted to a compound (13) of the present invention by treatment with ammonia in an inert solvent.

In this reaction, the inert solvent is, for example, an ether such as diethyl ether, tetrahydrofuran or dioxane; an alcohol such as methanol or ethanol; acetonitrile; or water.

(Reaction formulas 4)

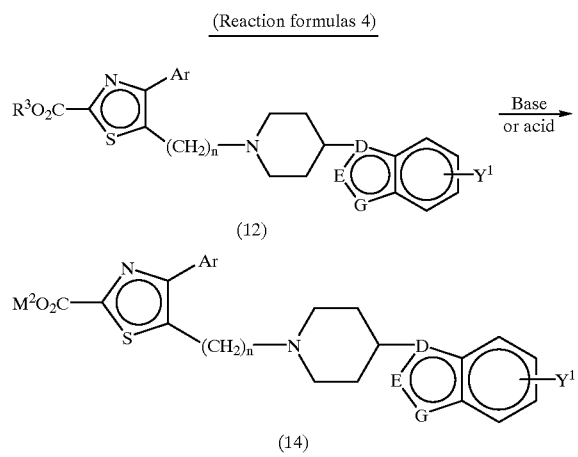

The ester group of a compound (12) is hydrolyzed in an inert solvent in the presence of a base or an acid to obtain a compound (14) of the present invention.

In this reaction, the inert solvent is, for example, an ether such as diethyl ether, tetrahydrofuran or dioxane; an alcohol such as methanol or ethanol; a ketone such as acetone; an organic carboxylic acid such as acetic acid; N,N-dimethylformamide; or water. The base is, for example, an inorganic base such as sodium hydroxide, potassium hydroxide, lithium hydroxide, barium hydroxide, calcium hydroxide or sodium carbonate. The acid is, for example, an inorganic acid such as hydrochloric acid, hydrobromic acid or sulfuric acid; or an organic acid such as trifluoroacetic acid, formic acid, p-toluenesulfonic acid or methanesulfonic acid.

(Reaction formulas 5)

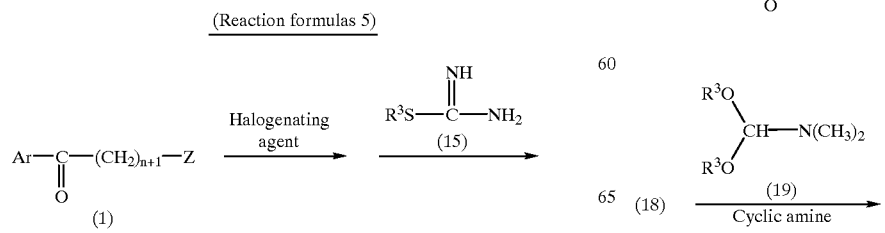

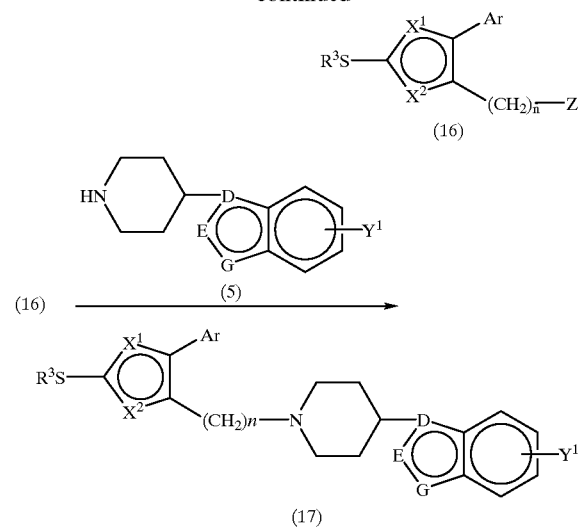

A ketone derivative (1) is halogenated with a halogenating agent in the same manner as in the reaction formulas 1 and reacted with an S-alkylisothiourea derivative (15) in an inert solvent in the presence of a base to obtain an imidazole derivative (16). Then, the compound (16) is reacted with a piperidine derivative (5) in an inert solvent in the presence of a base to obtain a compound (17) of the present invention.

In each of these reactions, the inert solvent is, for example, an alcohol such as ethanol or isopropanol; an ether such as tetrahydrofuran or dioxane; a hydrocarbon such as benzene or toluene; a ketone compound such as acetone or methyl ethyl ketone; N,N-dimethylformamide; acetonitrile; water; or a mixed solvent thereof. The base is, for example, an organic amine such as triethylamine, diisopropylethylamine or pyridine; an alcoholate such as sodium ethoxide; an alkali metal amide such as sodium amide; an inorganic base such as sodium hydrogencarbonate, sodium carbonate, potassium carbonate, sodium hydroxide or sodium hydride; or an organic acid salt such as sodium acetate.

(Reaction formulas 6)

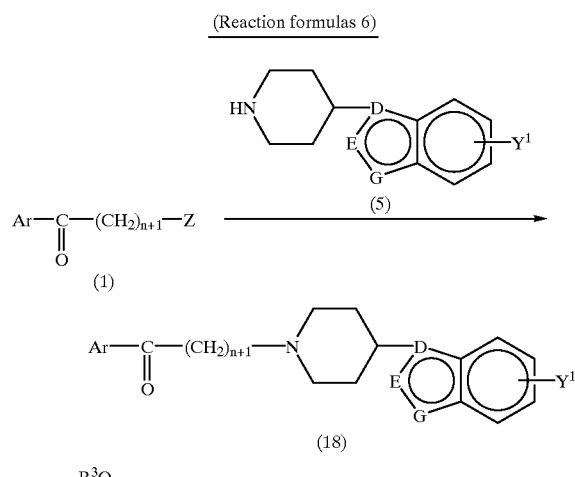

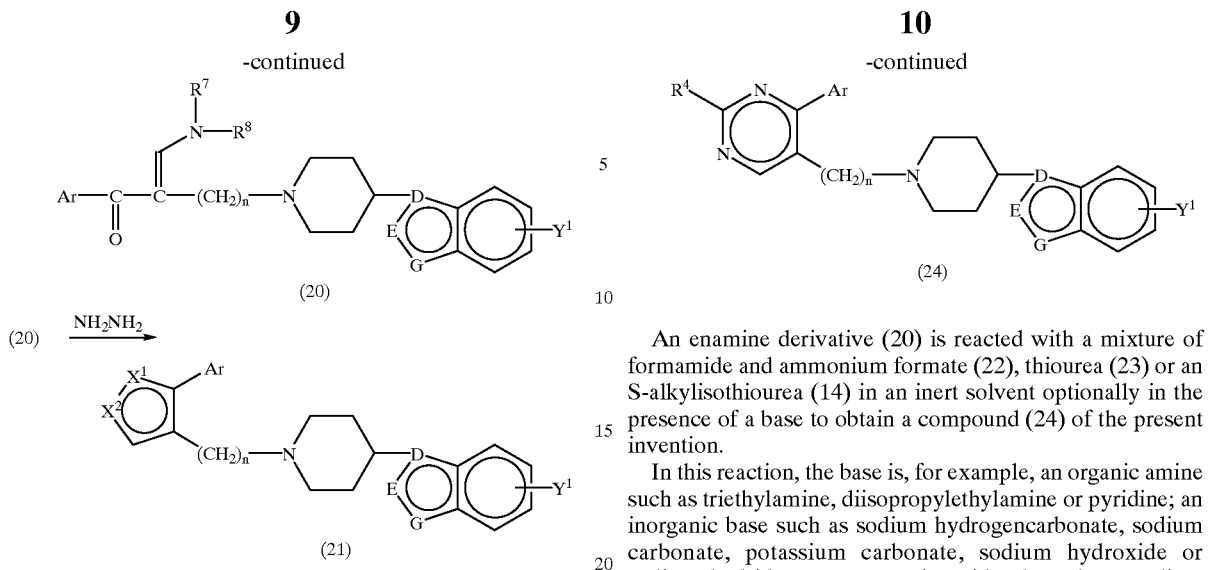

A ketone derivative (1) is reacted with a piperidine derivative (5) in an inert solvent or without a solvent in the presence or absence of a base to obtain an aminoketone (18).

In this reaction, the base is, for example, an organic amine such as triethylamine, diisopropylethylamine or pyridine; an inorganic base such as sodium hydrogencarbonate, sodium carbonate, potassium carbonate, sodium hydroxide or sodium hydride; or an organic acid salt such as sodium acetate. The inert solvent is, for example, an ether such as diethyl ether, tetrahydrofuran or dioxane; a hydrocarbon such as benzene or toluene; or an alcohol such as ethanol.

Then, the aminoketone (18) is reacted with an N,N-dimethylformamide dialkylacetal (19) in an inert solvent in the presence of a cyclic amine to obtain an enamine derivative (20), which is reacted with hydrazine to obtain a compound (21) of the present invention.

In the former reaction, the cyclicamine is, for example, pyrrolidine, piperidine, morpholine or N-methylpiperazine. The inert solvent is, for example, an ether such as tetrahydrofuran or dioxane; a hydrocarbon such as benzene or toluene; acetonitrile; or N,N-dimethylformamide. A solvent used in the reaction with hydrazine is, for example, an alcohol such as methanol, ethanol or isopropanol; an ether such as diethyl ether or tetrahydrofuran; a hydrocarbon such as toluene; N,N-dimethylformamide; acetonitrile; water; or a mixed solvent thereof.

(Reaction formulas 7)

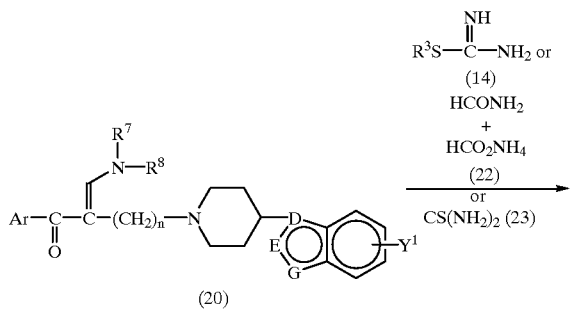

An enamine derivative (20) is reacted with a mixture of formamide and ammonium formate (22), thiourea (23) or an S-alkylisothiourea (14) in an inert solvent optionally in the presence of a base to obtain a compound (24) of the present invention.

In this reaction, the base is, for example, an organic amine such as triethylamine, diisopropylethylamine or pyridine; an inorganic base such as sodium hydrogencarbonate, sodium carbonate, potassium carbonate, sodium hydroxide or sodium hydride; or an organic acid salt such as sodium acetate. The inert solvent is, for example, an organic carboxylic acid such as acetic acid; an organic halide such as carbon tetrachloride or chloroform; an alcohol such as ethanol or isopropanol; an ether such as diethyl ether or tetrahydrofuran; a hydrocarbon such as toluene; N,N-dimethylformamide; acetonitrile; water; or a mixed solvent thereof.

The compound of the present invention has a high affinity for dopamine $D_4$ receptors but has a low affinity for dopamine $D_2$ receptors, namely, said compound has an excellent selectivity. Therefore, the compound of the present invention is useful as a prophylactic and therapeutic agent for diseases such as schizophrenia and problem behaviors associated with cerebrovascular diseases or senile dementia, and is useful as a drug that does not cause extrapyramidal diseases as side effects.

For the purposes described above, the compound of the present invention can be formulated into tablets, pills, capsules, granules, a powder, solution, emulsion, suspension, injection or the like by a conventional preparation technique by adding conventional additives such as an extender, binder, disintegrator, pH adjustor, solubilizer, etc.

The compound of the present invention can be administered to an adult patient orally or parenterally in a dose of 0.1 to 500 mg per day in one portion or several portions. The dose may be properly varied depending on the kind of a disease and the age, body weight and symptom of the patient.

BEST MODE FOR CARRYING OUT THE INVENTION

The present invention is concretely explained with the reference to the following examples and test example.

EXAMPLE 1

Production of 2-amino-5-(2-chloroethyl)-4-(4-fluorophenyl)thiazole hydrobromide (compound No. A-01)

In 40 ml of acetic acid was dissolved 10.03 g of 4-chloro-4'-fluorobutyrophenone, followed by adding thereto a drop of a 47% aqueous hydrobromic acid, and a solution of 8.07 g of bromine in 10 ml of acetic acid was added dropwise thereto over a period of 30 minutes. After the reaction mixture was stirred at room temperature for 1.5 hours, the acetic acid was distilled off under reduced pressure.

To the residue were added 50 ml of ethanol and 3.81 g of thiourea, and the resulting mixture was heated under reflux for 5 hours. The reaction mixture was concentrated under reduced pressure to obtain crystals, which were recrystallized from ethanol to obtain 11.62 g of 2-amino-5-(2-chloroethyl)-4-(4-fluorophenyl)thiazole hydrobromide.

M.p. 185.0–187.0° C.

Table A shows the structures and physical property data of this compound and compounds obtained in the same manner as above.

The free bases in Table A were obtained by neutralization with an aqueous sodium hydroxide solution or a saturated aqueous sodium hydrogencarbonate solution. If necessary, the free bases were purified by a silica gel column chromatography.

EXAMPLE 2

Production of 5-(2-chloroethyl)-4-(4-fluorophenyl) thiazole hydrochloride (compound No. A-10)

In 50 ml of carbon tetrachloride was dissolved 10.03 g of 4-chloro-4'-fluorobutyrophenone, and 8.68 g of bromine was added dropwise thereto over a period of 15 minutes. The reaction mixture was stirred at room temperature for 1.5 hours and then concentrated under reduced pressure.

The residue was added to a suspension of 2.36 g of formamide and 2.53 g of diphosphorus pentasulfide in 100 ml of dioxane which had been previously stirred with heating at 100° C. for 1.5 hours, and the resulting mixture was stirred with heating at 100° C. for 5 hours. The reaction mixture was concentrated under reduced pressure and neutralized with a saturated aqueous sodium hydrogencarbonate solution, followed by extraction with ethyl acetate. The extract solution was washed with a saturated aqueous sodium hydrogencarbonate solution and then a saturated aqueous sodium chloride solution, and dried over anhydrous sodium sulfate. After the drying agent was filtered off, the filtrate was concentrated under reduced pressure and purified by a flush column chromatography (silica gel: Wakogel C200, eluent: hexane-ethyl acetate=10:1). The free base thus obtained was treated with a 4N solution of hydrochloric acid in ethyl acetate and then recrystallized from isopropanol to obtain 3.10 g of 5-(2-chloroethyl)-4-(4-fluorophenyl) thiazole hydrochloride.

M.p. 114.5–116.5° C.

Table A shows the structure and physical property datum of this compound.

EXAMPLE 3

Production of 2-hydroxy-5-(2-chloroethyl)-4-(4-fluorophenyl)thiazole (compound No. A-11)

In 80 ml of chloroform was dissolved 20.08 g of 4-chloro-4'-fluorobutyrophenone, and a solution of 5.2 ml of bromine in 10 ml of chloroform was added dropwise thereto over a period of 30 minutes. The mixture was stirred at room temperature for 1 hour and then concentrated under reduced pressure.

The residue was dissolved in 120 ml of ethanol, followed by adding thereto 9.80 g of potassium thiocyanate, and the resulting mixture was heated under reflux with stirring for 1 hour. After the reaction solution was concentrated under reduced pressure, water was added to the residue, followed by extraction with ethyl acetate. The extract solution was washed with water and a saturated aqueous sodium chloride solution and then dried over anhydrous sodium sulfate, after which the drying agent was filtered off, and the filtrate was concentrated under reduced pressure.

The residue was heated under reflux with stirring for 3 hours in a mixture of 140 ml of acetic acid, 40 ml of water and 15 ml of sulfuric acid. After the reaction solution was concentrated under reduced pressure, the residue was poured into ice water, followed by extraction with ethyl acetate. The extract solution was washed with water, a saturated aqueous sodium hydrogencarbonate solution and a saturated aqueous sodium chloride solution and then dried over anhydrous sodium sulfate, after which the drying agent was filtered off. The filtrate was concentrated under reduced pressure, and isopropyl ether was added to the residue to cause crystallization, followed by recrystallization from hexane-ethyl acetate, whereby 16.40 g of 2-hydroxy-5-(2-chloroethyl)-4-(4-fluorophenyl)thiazole was obtained.

M.p. 140.0–141.5° C.

Table A shows the structure and physical property datum of this compound.

EXAMPLE 4

Production of ethyl 5-(2-chloroethyl)-4-(4-fluorophenyl)-2-thiazolecarboxylate (compound No. A-12)

In 250 ml of carbon tetrachloride was dissolved 50.00 g of 4-chloro-4'-fluorobutyrophenone, and 41.30 g of bromine was added dropwise thereto over a period of 30 minutes. The mixture was stirred at room temperature for 1 hour and then concentrated under reduced pressure.

The residue and 33.20 g of ethyl thiooxamate were stirred in 250 ml of ethanol with heating under reflux for 15 hours. The reaction mixture was concentrated under reduced pressure, and ethyl acetate was added to the residue, after which the resulting mixture was washed with a saturated aqueous sodium hydrogencarbonate solution and then a saturated aqueous sodium chloride solution, and dried over anhydrous sodium sulfate. The drying agent was filtered off, and the filtrate was concentrated under reduced pressure. The residue was purified by a flush column chromatography (silica gel: Wakogel C200, eluent: hexane-ethyl acetate= 10:1 to 9:1) and then recrystallized from diisopropyl ether to obtain 29.14 g of ethyl 5-(2-chloroethyl)-4-(4-fluorophenyl)-2-thiazolecarboxylate.

M.p. 81.5–82.5° C.

Table A shows the structures and physical property data of this compound and compounds obtained in the same manner as above.

EXAMPLE 5

Production of 2-methylthio-4-(2-chloroethyl)-5-(4-fluorophenyl)imidazole 2-methylthio-5-(2-chloroethyl)-4-(4-fluorophenyl)imidazole (compound No. A-15)

In 5 ml of chloroform was dissolved 2.00 g of 4-chloro-4'-fluorobutyrophenone, and a solution of 0.52 ml of bromine in 1 ml of chloroform was added dropwise thereto over a period of 5 minutes. The reaction mixture was stirred at room temperature for 1 hour and then concentrated under reduced pressure.

The residue was dissolved in 20 ml of N,N-dimethylformamide, followed by adding thereto 3.50 g of S-methylisothiourea hydrochloride, 2.76 g of anhydrous potassium carbonate and 0.15 g of sodium iodide, and the resulting mixture was stirred with heating at 80° C. for 1 hour. The reaction solution was poured into ice water, followed by extraction with diethyl ether. The extract solution was washed with water and a saturated aqueous sodium chloride solution and then dried over anhydrous sodium sulfate, after which the drying agent was filtered off, and the filtrate was concentrated under reduced pressure. The residue was purified by a flush column chromatography (silica gel: Wakogel C200, eluent: hexane-ethyl acetate=2:1) and then recrystallized from isopropyl ether to obtain 1.13 g of 2-methylthio-4-(2-chloroethyl)-5-(4-fluorophenyl) imidazole [2-methylthio-5-(2-chloroethyl)-4-(4-fluorophenyl)imidazole].

M.p. 134.0–135.0° C.

EXAMPLE 6

Production of 2-amino-4-(4-fluorophenyl)-5-[2-[4-(6-fluorobenzofuran-3-yl)piperidin-1-yl]ethyl]thiazole (compound No. B-01)

A mixture of 0.917 g of 2-amino-5-(2-bromoethyl)-4-(4-fluorophenyl)thiazole hydrobromide, 0.511 g of 4-(6-fluorobenzofuran-3-yl)piperidine hydrochloride, 1.5 ml of diisopropylethylamine and 3 ml of methanol was stirred with heating under reflux for 12 hours. The reaction mixture was cooled to room temperature and then poured into water, followed by extraction with chloroform. The extract solution was dried over magnesium sulfate, and then the solvent was distilled off under reduced pressure, after which ether was added to the residue and the crystals were collected by filtration. The crystals were recrystallized from ethanol to obtain 0.57 g of 2-amino-4-(4-fluorophenyl)-5-[2-[4-(6-fluorobenzofuran-3-yl)piperidin-1-yl]ethyl]thiazole.

M.p. 162.0–164.0° C.

Table B shows the structures and physical property data of this compound and compounds obtained in the same manner as above.

If necessary, these compounds were purified by a silica gel column chromatography.

EXAMPLE 7

Production of 2-amino-4-(4-fluorophenyl)-5-[2-[4-(5-fluoro-1H-benzotriazol-1-yl)piperidin-1-yl]ethyl]thiazole (compound No. B-26)

A mixture of 0.917 g of 2-amino-5-(2-bromoethyl)-4-(4-fluorophenyl)thiazole hydrobromide, 0.441 g of 4-(5-fluoro-1H-benzotriazol-1-yl)piperidine, 1 ml of diisopropylethylamine and 4 ml of methanol was stirred with heating under reflux for 12 hours. After the reaction mixture was cooled to room temperature, ethanol was added thereto and the crystals were collected by filtration. The crystals were recrystallized from chloroform-ethanol to obtain 0.56 g of 2-amino-4-(4-fluorophenyl)-5-[2-[4-(5-fluoro-1H-benzotriazol-1-yl)piperidin-1-yl]ethyl]thiazole.

M.p. 234.0–235.0° C.

Table B shows the structures and physical property data of this compound and compounds obtained in the same manner as above.

EXAMPLE 8

Production of 2-hydroxy-4-(4-fluorophenyl)-5-[2-[4-(6-fluorobenzofuran-3-yl)piperidin-1-yl]ethyl]thiazole (compound No. B-06)

A mixture of 0.134 g of 5-(2-chloroethyl)-2-hydroxy-4-(4-fluorophenyl)thiazole, 0.11 g of 4-(6-fluorobenzofuran-3-yl)piperidine hydrochloride, 0.28 ml of diisopropylethylamine and 0.5 ml of methanol was stirred with heating under reflux for 15 hours. After the reaction mixture was cooled to room temperature, the solvent was distilled off under reduced pressure, and the residue was purified by a flush chromatography (silica gel: Merckkieselgel 60 230- to 400-mesh, eluent: hexane-ethyl acetate=2:1). The purified product was recrystallized from ethyl acetate-hexane to obtain 0.066 g of 2-hydroxy-4-(4-fluorophenyl)-5-[2-[4-(6-fluorobenzofuran-3-yl)piperidin-1-yl]ethyl]thiazole.

M.p. 186.0–188.0° C.

Table B shows the structures and physical property data of this compound and compounds obtained in the same manner as above.

EXAMPLE 9

Production of 2-methylthio-4-(4-fluorophenyl)-5-[2-[4-(5-fluoro-1H-benzotriazol-1-yl)piperidin-1-yl]ethyl]imidazole 2-methylthio-5-(4-fluorophenyl)-4-[2-[4-(5-fluoro-1H-benzotriazol-1-yl)piperidin-1-yl]ethyl]imidazole (compound No. C-03)

A mixture of 0.141 g of 2-methylthio-4-(2-chloroethyl)-5-(4-fluorophenyl)imidazole, 2-methylthio-5-(2-chloroethyl)-4-(4-fluorophenyl)imidazole, 0.095 g of 4-(5-fluoro-1H-benzotriazol-1-yl)piperidine, 0.19 ml of diisopropylethylamine and 0.6 ml of methanol was stirred with heating under reflux for 17 hours. After the mixture was cooled to room temperature, the solvent was distilled off under reduced pressure, and the residue was purified by a flush chromatography (silica gel: Chromatorex NHDM1020, eluent: hexane-ethyl acetate=1:3). The purified product was recrystallized from ethanol-hexane to obtain 0.104 g of 2-methylthio-4-(4-fluorophenyl)-5-[2-[4-(5-fluoro-1H-benzotriazol-1-yl)piperidin-1-yl]ethyl]imidazole {2-methylthio-5-(4-fluorophenyl)-4-[2-[4-(5-fluoro-1H-benzotriazol-1-yl)piperidin-1-yl]ethyl]imidazole}.

M.p. 223.0–224.0° C.

Table C shows the structures and physical property data of this compound and compounds obtained in the same manner as above.

EXAMPLE 10

Production of 5-(4-fluorophenyl)-4-[2-[4-(6-fluorobenzo[b]thiophen-3-yl)piperidin-1-yl]ethyl]pyrazole 3-(4-fluorophenyl)-4-[2-[4-(6-fluorobenzo[b]thiophen-3-yl)piperidin-1-yl]ethyl]pyrazole.

(1) A mixture of 1.5 g of 2-(4-fluorophenyl)-2-(3-chloropropyl)-1,3-dioxolane, 1.5 g of 4-(6-fluorobenzo[b]thiophen-3-yl)piperidine hydrochloride, 3.3 ml of diisopropylethylamine and 2.5 ml of methanol was stirred with heating under reflux for 25 hours. The reaction mixture was separated with chloroform and a saturated aqueous sodium hydrogencarbonate solution, and the aqueous layer was extracted with chloroform. The combined organic layer was washed with water and a saturated aqueous sodium chloride solution and then dried over magnesium sulfate. The solvent was distilled off under reduced pressure, and the residue was purified by a flush chromatography (silica gel: Merckkieselgel 60 230-to 400-mesh, eluent: hexane-ethyl acetate= 1:2) to obtain 0.71 g of 2-(4-fluorophenyl)-2-[3-[4-(6-fluorobenzo[b]thiophen-3-yl)piperidin-1-yl]propyl]-1,3-dioxolane.

This compound was stirred at room temperature for 20 hours in a mixture of 3 ml of 1N hydrochloric acid and 4 ml of tetrahydrofuran. After the solvent was distilled off under reduced pressure, the residue was separated with ethyl acetate and a saturated aqueous sodium hydrogencarbonate solution, and the aqueous layer was extracted with ethyl acetate. The combined organic layer was washed with water and a saturated aqueous sodium chloride solution and then dried over magnesium sulfate. The solvent was distilled off under reduced pressure, and the residue was dissolved in 20 ml of ethyl acetate and treated with 1 ml of a 4N hydrogen chloride/1,4-dioxane solution to obtain 0.54 g of 6-fluoro-3-[1-[4-(4-fluorophenyl)-4-oxobutyl]piperidin-4-yl]benzo[b]thiophene hydrochloride.

(2) A mixture of 0.15 g of 6-fluoro-3-[1-[4-(4-fluorophenyl)-4-oxobutyl]piperidin-4-yl]benzo[b]thiophene hydrochloride, 0.05 g of anhydrous potassium carbonate, 0.36 ml of N,N-dimethylformamide dimethyl acetal, 0.25 ml of pyrrolidine and 0.5 ml of N,N-dimethylformamide was stirred on an oil bath at 120° C. for 3.5 hours. The reaction mixture was cooled to room temperature and then separated with ethyl acetate and water, and the aqueous layer was extracted with ethyl acetate. The combined organic layer was washed three times with a saturated aqueous sodium chloride solution. After drying over magnesium sulfate, the solvent was distilled off under reduced pressure to obtain crude 6-fluoro-3-[1-[3-(1-pyrrolidinomethylene)-4-(4-fluorophenyl)-4-oxobutyl]piperidin-4-yl]benzo[b]thiophene.

This compound was dissolved in 2 ml of methanol, followed by adding thereto 0.3 ml of a 80% aqueous hydrazine solution, and the resulting mixture was heated under reflux for 2 hours. The reaction mixture was cooled to room temperature and then separated with a saturated aqueous sodium hydrogencarbonate solution and ethyl acetate, and the aqueous layer was extracted with ethyl acetate. The combined organic layer was washed with water and a saturated aqueous sodium chloride solution. After drying over magnesium sulfate, the solvent was distilled off under reduced pressure, and the residue was purified by a column chromatography (silica gel: Chromatorex NHDM1020, eluent: hexane-ethyl acetate 1:2). The purified product was recrystallized from ethyl acetate-ether to obtain 0.02 g of 5-(4-fluorophenyl)-4-[2-[4-(6-fluorobenzo[b]thiophen-3-yl)piperidin-1-yl]ethyl]pyrazole {3-(4-fluorophenyl)-4-[2-[4-(6-fluorobenzo[b]thiophen-3-yl)piperidin-1-yl]ethyl]pyrazole}.

M.p. 162.0–163.0° C.

EXAMPLE 11

Production of 6-(4-fluorophenyl)-5-[2-[4-(6-fluorobenzo[b]thiophen-3-yl)piperidin-1-yl]ethyl]pyrimidine.

After 3.6 ml of formamide, 0.4 g of ammonium formate and 0.1 ml of water were added to crude 6-fluoro-3-[1-[3-(1-pyrrolidinomethylene)-4-(4-fluorophenyl)-4-oxobutyl] piperidin-4-yl]benzo[b]thiophene obtained from 0.35 g of 6-fluoro-3-[1-[4-(4-fluorophenyl)-4-oxobutyl]piperidin-4-yl]benzo[b]thiophene hydrochloride by the same procedure as in Example 10, the mixture was stirred with heating at 180° C. for 1.5 hours. The reaction mixture was cooled to room temperature and then separated with a saturated aqueous sodium hydrogencarbonate solution and ethyl acetate, and the aqueous layer was extracted with ethyl acetate. The combined organic layer was washed with water and a saturated aqueous sodium chloride solution. After drying over magnesium sulfate, the solvent was distilled off under reduced pressure, and the residue was purified by a column chromatography (silica gel: Chromatorex NHDM1020, eluent: hexane-ethyl acetate=2:1). The purified product was recrystallized from ether to obtain 0.04 g of 6-(4-fluorophenyl)-5-[2-[4-(6-fluorobenzo[b]thiophen-3-yl)piperidin-1-yl]ethyl]pyrimidine.

M.p. 123.0–124.0° C.

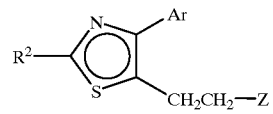

TABLE A

| Compound No. | $R^2$ | Ar | Z | Salt | m.p. (° C.) (Solvent for recrystallization)*[1] |
|---|---|---|---|---|---|
| A-01 | $NH_2$ | 4-F—Ph | Cl | HBr | 185.0–187.0 (EtOH) |
| A-02 | $NH_2$ | 4-F—Ph | Br | HBr | 162.0–164.0 (EtOH) |
| A-03 | $NH_2$ | 4-Cl—Ph | Cl | HBr | 203.0–205.0 (EtOH) |
| A-04 | $NH_2$ | 4-Me—Ph | Cl | HBr | 183.0–184.5 (EtOH) |
| A-05 | $NH_2$ | Ph | Cl |  | 128.0–129.0 (PhCH$_3$) |
| A-06 | NHMe | 4-F—Ph | Cl | HCl | 125.0–126.5 (IPA) |
| A-07 | Me | 4-F—Ph | Cl | HCl | 122.5–123.5 (IPA) |
| A-08 | Me | 4-Me—Ph | Cl | HCl | 141.0–143.0 (IPA) |
| A-09 | Me | Ph | Cl | HCl | 111.5–113.0 (IPE) |
| A-10 | H | 4-F—Ph | Cl | HCl | 114.5–116.5 (IPA) |
| A-11 | OH | 4-F—Ph | Cl |  | 140.0–141.5 (Hex-AcOEt) |
| A-12 | $CO_2Et$ | 4-F—Ph | Cl |  | 81.5–82.5 (IPE) |
| A-13 | $CO_2Et$ | 4-MePh | Cl |  | 79.0–80.0 (IPE) |
| A-14 | $CO_2Et$ | Ph | Cl |  | Oil*[2] |

*[1]solvent for recrystallization; EtOH = Ethanol, PhCH$_3$ = toluene, IPA = isopropyl alcohol, IPE = diisopropyl ether, Hex = hexane, AcOEt = ethyl acetate
*[2]NMR(CDCl$_3$)δ (ppm); 1.44(3H, t), 3.44(2H, d), 3.74(2H, d), 4.49(2H, q), 7.38–7.64(4H, m)

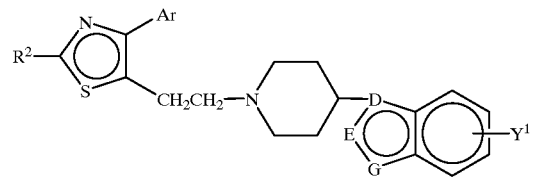

TABLE B

| Compound No. | $R^2$ | Ar | D | E | G | $Y^1$ | m.p.(° C.) (Solvent for recrystallization)*[1] |
|---|---|---|---|---|---|---|---|
| B-01 | $NH_2$ | 4-F—Ph | C | CH | O | 6-F | 210.0–211.0 (EtOH) |
| B-02 | $NH_2$ | Ph | C | CH | O | 6-F | 199.0–201.0 (AcOEt-Hex) |
| B-03 | Me | 4-F—Ph | C | CH | O | 6-F | 121.0–123.0 (Ether) |
| B-04 | Me | Ph | C | CH | O | 6-F | 103.0–105.0 (AcOEt-Hex) |
| B-05 | H | 4-F—Ph | C | CH | O | 6-F | 130.0–132.0 (AcOEt- |

TABLE B-continued

| Compound No. | R² | Ar | D | E | G | Y¹ | m.p.(° C.) (Solvent for recrystallization)*¹ |
|---|---|---|---|---|---|---|---|
| B-06 | OH | 4-F—Ph | C | CH | O | 6-F | 186.0–188.0 (AcOEt-Hex) |
| B-07 | CONH₂ | 4-F—Ph | C | CH | O | 6-F | 199.0–201.0 (EtOH) |
| B-08 | NH₂ | Ph | C | CH | S | 6-F | 216.0–218.0 (CHCl₃—EtOH) |
| B-09 | NH₂ | 4-F—Ph | C | CH | NH | H | 203.0–203.5 (EtOH) |
| B-10 | NH₂ | 4-Me—Ph | C | CH | NH | H | 99.0–101.0 (AcOEt-Ether) |
| B-11 | Me | 4-F—Ph | C | CH | NH | H | 165.0–167.0 (AcOEt-Hex) |
| B-12 | Me | 4-F—Ph | C | CH | NH | 6-F | 190.0–191.0 (AcOEt-Ether) |
| B-13 | Me | 4-Me—Ph | C | CH | NH | H | 138.0–141.0 (Ether) |
| B-14 | H | 4-F—Ph | C | CH | NH | H | 141.0–143.0 (AcOEt-Ether) |
| B-15 | MeNH | 4-F—Ph | C | CH | NH | H | 173.0–175.0 (Ether) |
| B-16 | CO₂Et | 4-F—Ph | C | CH | NH | H | 184.0–186.0 (EtOH) |
| B-17 | CO2Me | 4-Me—Ph | C | CH | NH | H | 194.0–196.0 (AcOEt-Ether) |
| B-18 | CO₂Me | Ph | C | CH | NH | H | 182.0–183.0 (Ether) |
| B-19 | CONH₂ | 4-F—Ph | C | CH | NH | H | 206.0–209.0 (AcOEt-Ether) |
| B-20 | CONH₂ | 4-F—Ph | C | CH | NH | 6-F | 208.0–209.5 (AcOEt-Ether) |
| B-21 | NH₂ | 4-F—Ph | C | N | O | 6-F | 208.0–209.0 (EtOH-Hex) |
| B-22 | Me | 4-F—Ph | C | N | O | 6-F | 102.0–103.0 (EtOH-Hex) |
| B-23 | NH₂ | 4-F—Ph | C | N | S | 6-F | 203.0–204.0 (EtOH) |
| B-24 | NH₂ | 4-F—Ph | C | N | NH | 6-F | 104.0–106.0 (EtOH) |
| B-25 | NH₂ | 4-F—Ph | N | CH | N | 5-F | 282.0–284.0 (CHCl₃—EtOH) |
| B-26 | NH₂ | 4-F—Ph | N | N | N | 5-F | 234.0–235.0 (CHCl₃—EtOH) |
| B-27 | NH₂ | 4-Cl—Ph | N | N | N | 5-F | 225.0–227.0 (CHCl₃—EtOH) |
| B-28 | Me | 4-F—Ph | N | N | N | H | 122.0–123.Q (Ether-Hex) |
| B-29 | Me | 4-F—Ph | N | N | N | 5-F | 145.0–146.0 (AcOEt-Hex) |
| B-30 | H | 4-F—Ph | N | N | N | 5-F | 144.0–146.0 (AcOEt-Hex) |

*¹solvent for recrystallization; EtOH = ethanol, AcOEt = ethyl acetate, Hex = hexane, CHCl₃ = chloroform

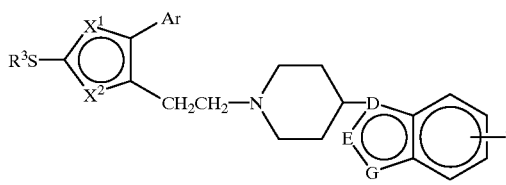

TABLE C

| Compound No. | R³ | X¹*² | X²*² | Ar | D | E | G | Y¹ | m.p.(° C. (Solvent for recrystallization)*¹ |
|---|---|---|---|---|---|---|---|---|---|
| C-01 | Me | N | NH | 4-F—Ph | C | CH | O | 6-F | 151.0–152.0 (AcOEt-Ether) |
| C-02 | Me | N | NH | 4-F—Ph | C | CH | NH | H | 111.0–114.0 (AcOEt-Ether) |
| C-03 | Me | N | NH | 4-F—Ph | N | N | N | 5-F | 223.0–224.0 (EtOH-Hex) |

*¹solvent for recrystallization; CHCl₃ = chloroform, EtOH = ethanol, AcOEt = ethyl acetate, Hex = hexane
*²Only one of imidazole tautomers is listed.

Test Example

[Receptor Binding Assay]

1. Dopamine $D_4$ Receptor Binding Assay

Chinese hamster ovarium (CHO) cell membrane wherein human $D_{4.2}$ receptor was expressed was used as a receptor preparation.

[³H] spiperone was used as a [³H]-labeled ligand.

Binding reaction using [³H]-labeled ligand was carried out by the following method described in Eur. J. Pharmacol., 233, 173(1993).

Human $D_{4.2}$ receptor binding assay: The (CHO) cell membrane wherein human $D_{4.2}$ receptor was expressed, [³H] spiperone (0.5 nM) and each test drug were incubated at 27° C. for 2 hours in 50 mM Tris-hydrochloric acid buffer (pH 7.4) containing 5 mM EDTA,: 1.5 mM calcium chloride, 5mM potassium chloride and 120 mM sodium chloride.

After completion of the reaction, the reaction mixture was filtered by suction through a glass filter (GF/B), and radioactivity in the filter paper was measured with a liquid scintillation spectrometer.

Binding under the reaction of [³H] spiperone carried out in the presence of 10 μM haloperidol was defined as nonspecific binding of [³H] spiperone, and the difference between the total binding and the nonspecific binding was defined as specific binding. An inhibition curve was obtained by reacting a definite concentration of [³H] spiperone with various concentrations of each test drug under the above conditions, and a concentration of the test drug at which the test drug inhibited binding of [³H] spiperone by 50% ($IC_{50}$) was determined. The results are shown in Table D.

2. Dopamine $D_2$ Receptor Binding Assay

Rat striatum membrane was used as a receptor preparation.

[³H] raclopride was used as a [³H]-labeled ligand.

Binding reaction using [³H]-labeled ligand was carried out by the following method described in Mol., Pharmacol., 43, 749(1993).

Preparation of the receptor preparation: Rat striatum was homogenized in 50 mM Tris-hydrochloric acid buffer (pH 7.4), and the homogenate was centrifuged at 48,000×g and the pellet was washed once with Tris-hydrochloric acid buffer. The washed pellet was suspended in 50 mM Tris-hydrochloric acid buffer (pH 7.4) containing 120 mM sodium chloride, 5mM potassium chloride, 2 mM calcium chloride and 1 mM magnesium chloride, to obtain a membrane preparation.

Dopamine $D_2$ receptor binding assay: The membrane preparation (0.5 mg protein/ml), [³H] raclopride (1 nM) and each test drug were incubated at 25° C. for 1 hour.

After completion of the reaction, the reaction mixture was filtered by suction through a glass filter (GF/B), and radioactivity in the filter paper was measured with a liquid scintillation spectrometer.

Binding under the reaction of [³H] raclopride carried out in the presence of 10 μM haloperidol was defined as nonspecific binding of [³H] lacropirido, and the difference between the total binding and the nonspecific binding was defined as specific binding. An inhibition curve was obtained by reacting a definite concentration of [³H] raclopride with various concentrations of each test drug under the above conditions, and a concentration of the test drug at which the test drug inhibited binding of [³H] raclopride by 50% ($IC_{50}$) was determined. The results are shown in Table D.

TABLE D

| Compound No. | $IC_{50}$ (nM) | |
| --- | --- | --- |
|  | $D_4$ | $D_2$ |
| B-01 | 3.1 | 67.3 |
| B-09 | 2.0 | 81.1 |
| B-11 | 0.4 | 26.6 |
| B-25 | 32.0 | >1000 |
| B-26 | 5.5 | 298.4 |
| B-29 | 2.4 | 205.7 |
| Clozapine | 130.0 | 394.4 |

INDUSTRIAL APPLICABILITY

The compound of the present invention has a high affinity for dopamine $D_4$ receptors but has a low affinity for dopamine $D_2$ receptors, namely, said compound has an excellent distinguishing capability.

Therefore, the compound of the present invention is useful as a prophylactic and therapeutic agent for diseases such as schizophrenia and problem behaviors associated with cerebrovascular diseases or senile dementia, and is useful as a drug that does not cause extrapyramidal diseases as side effects.

What is claimed is:

1. An arylpiperidine compound represented by the formula (I):

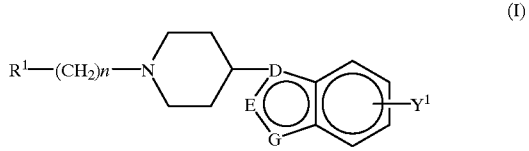

(wherein D is a carbon atom, E is a CH group, G is an oxygen atom, a sulfur atom, a nitrogen atom or an NH group, $Y^1$ is a hydrogen atom, n is an integer of 1 to 4, and $R^1$ is a group represented by the formula (i):

(wherein $R^2$ is a hydrogen atom, an alkyl group of 1 to 5 carbon atoms, an amino group, a monoalkylamino group of 1 to 5 carbon atoms, a hydroxyl group, an alkoxycarbonyl group of 2 to 6 carbon atoms, a carbamoyl group, a carboxyl group, or a metal salt of carboxyl group, and Ar is a substituted or unsubstituted phenyl group or a thienyl group) or a pharmaceutically acceptable salt thereof.

2. An arylpiperidine compound represented by the formula (III):

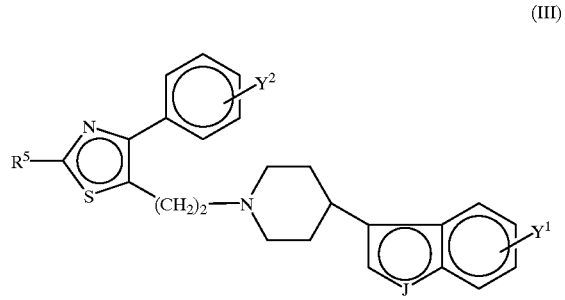

(wherein each of $Y^1$ is a hydrogen atom, $Y^2$ is a hydrogen atom or a halogen atom, $R^5$ is an alkyl group of 1 to 5 carbon atoms, an amino group or a carbamoyl group, and J is an oxygen atom, a sulfur atom or an NH group) or a pharmaceutically acceptable salt thereof.

3. A pharmaceutical composition comprising the arylpiperidine compound or the pharmaceutically acceptable salt thereof according to any one of claims 1, 2.

4. A pharmaceutical composition for antagonizing a dopamine $D_4$ receptor, comprising the arylpiperidine compound in an effective amount or a pharmaceutically acceptable salt thereof according to any one of claims 1, 2 as the active ingredient.

5. An arylpiperidine compound represented by the formula (I):

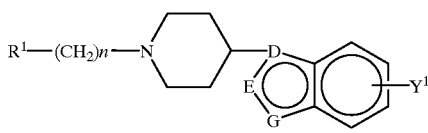

(wherein D is a carbon atom, E is a CH group, G is an oxygen atom, a sulfur atom, a nitrogen atom or an NH group, $Y^1$ is a halogen atom, n is an integer of 1 to 4, and $R^1$ is a group represented by the formula (i):

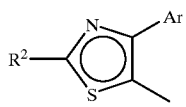

(wherein $R^2$ is a hydrogen atom, an alkyl group of 1 to 5 carbon atoms, an amino group, a monoalkylamino group of 1 to 5 carbon atoms, a hydroxyl group, an alkoxycarbonyl group of 2 to 6 carbon atoms, a carbamoyl group, a carboxyl group, or a metal salt of carboxyl group, and Ar is a substituted or unsubstituted phenyl group or a thienyl group)) or a pharmaceutically acceptable salt thereof.

6. An arylpiperidine compound represented by the formula (I):

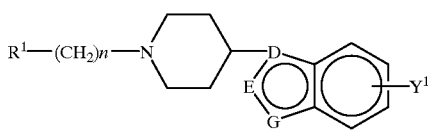

(wherein D is a carbon atom, E is a CH group, G is an oxygen atom, a sulfur atom, a nitrogen atom or an NH group, $Y^1$ is a hydrogen atom, n is an integer of 1 to 4, and $R^1$ is a group represented by the formula (ii):

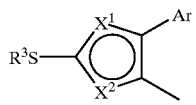

(wherein $R^3$ is an alkyl group of 1 to 5 carbon atoms, each of $X^1$ and $X^2$, which are different from each other, is a nitrogen atom or an NH group, and Ar is a substituted or unsubstituted phenyl group or a thienyl group)) or a pharmaceutically acceptable salt thereof.

7. An arylpiperidine compound represented by the formula (I):

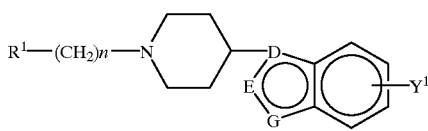

(wherein D is a carbon atom, E is a CH group, G is an oxygen atom, a sulfur atom, a nitrogen atom or an NH group, $Y^1$ is a halogen atom, n is an integer of 1 to 4, and $R^1$ is a group represented by the formula (ii):

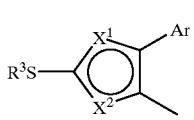

(wherein $R^3$ is an alkyl group of 1 to 5 carbon atoms, each of $X^1$ and $X^2$, which are different from each other, is a nitrogen atom or an NH group, and Ar is a substituted or unsubstituted phenyl group or a thienyl group)) or a pharmaceutically acceptable salt thereof.

8. An arylpiperidine compound represented by the formula (I):

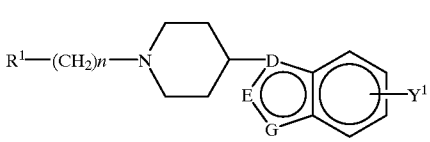

(wherein D is a carbon atom, E is a CH group, G is an oxygen atom, a sulfur atom, a nitrogen atom or an NH group, $Y^1$ is a hydrogen atom, n is an integer of 1 to 4, and $R^1$ is a group represented by the formula (iii):

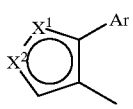

(wherein each of $X^1$ and $X^2$, which are different from each other, is a nitrogen atom or an NH group, and Ar is a substituted or unsubstituted phenyl group or a thienyl group)) or a pharmaceutically acceptable salt thereof.

9. An arylpiperidine compound represented by the formula (I):

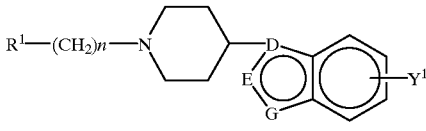

(wherein D is a carbon atom, E is a CH group, G is an oxygen atom, a sulfur atom, a nitrogen atom or an NH group, $Y^1$ is a halogen atom, n is an integer of 1 to 4, and $R^1$ is a group represented by the formula (iii):

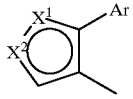

(wherein each of $X^1$ and $X^2$, which are different from each other, is a nitrogen atom or an NH group, and Ar is a substituted or unsubstituted phenyl group or a thienyl group)) or a pharmaceutically acceptable salt thereof.

10. An arylpiperidine compound represented by the formula (I):

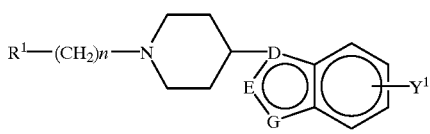

(wherein D is a carbon atom, E is a CH group, G is an oxygen atom, a sulfur atom, a nitrogen atom or an NH group, $Y^1$ is a hydrogen atom, n is an integer of 1 to 4, and $R^1$ is a group represented by the formula (iv):

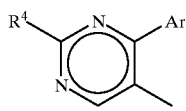

(wherein $R^4$ is a hydrogen atom, a mercapto group, or an alkylthio group of 1 to 5 carbon atoms, and Ar is a substituted or unsubstituted phenyl group or a thienyl group)) or a pharmaceutically acceptable salt thereof.

11. An arylpiperidine compound represented by the formula (I):

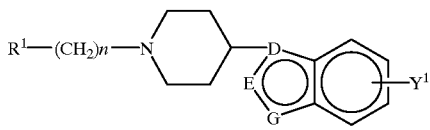

(wherein D is a carbon atom, E is a CH group, G is an oxygen atom, a sulfur atom, a nitrogen atom or an NH group, $Y^1$ is a halogen atom, n is an integer of 1 to 4, and $R^1$ is a group represented by the formula (iv):

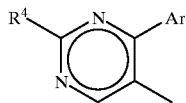

(wherein $R^4$ is a hydrogen atom, a mercapto group, or an alkylthio group of 1 to 5 carbon atoms, and Ar is a substituted or unsubstituted phenyl group or a thienyl group)) or a pharmaceutically acceptable salt thereof.

12. An arylpiperidine compound represented by the formula (II):

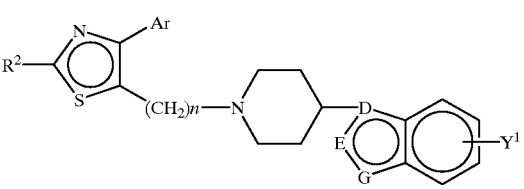

(wherein D is a carbon atom, E is a CH group, G is an oxygen atom, a sulfur atom, a nitrogen atom or an NH group, $Y^1$ is a halogen atom, n is an integer of 1 to 4, $R^2$ is a hydrogen atom, an alkyl group of 1 to 5 carbon atoms, an amino group, a monoalkylamino group of 1 to 5 carbon atoms, a hydroxyl group, an alkoxycarbonyl group of 2 to 6 carbon atoms, a carbamoyl group, a carboxyl group, or a metal salt of carboxyl group, and Ar is a substituted or unsubstituted phenyl group or a thienyl group) or a pharmaceutically acceptable salt thereof.

13. An arylpiperidine compound represented by the formula (III):

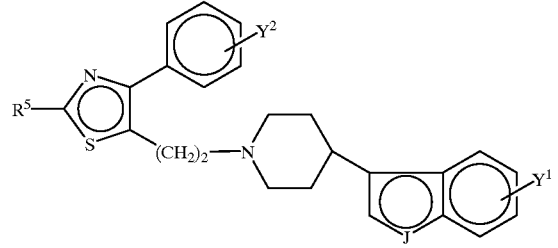

(wherein $Y^1$ is halogen, $Y^2$ is a hydrogen atom or a halogen atom, $R^5$ is an alkyl group of 1 to 5 carbon atoms, an amino group or a carbamoyl group, and J is an oxygen atom, a sulfur atom or an NH group) or a pharmaceutically acceptable salt thereof.

* * * * *